(12) United States Patent
Rasmussen et al.

(10) Patent No.: US 7,357,045 B2
(45) Date of Patent: Apr. 15, 2008

(54) BUOYANCY-CORRECTED GRAVIMETRIC ANALYSIS SYSTEM

(75) Inventors: Patricia E. Rasmussen, Ottawa (CA); David J. MacIntyre, East-Aldfield (CA); Josée Guénette, East-Aldfield (CA)

(73) Assignee: Her Majesty the Queen in Right of Canada as represented by The Minister of Health, Ottawa (CA)

( * ) Notice: Subject to any disclaimer, the term of this patent is extended or adjusted under 35 U.S.C. 154(b) by 344 days.

(21) Appl. No.: 11/113,271

(22) Filed: Apr. 25, 2005

(65) Prior Publication Data

US 2006/0021454 A1 Feb. 2, 2006

Related U.S. Application Data

(60) Provisional application No. 60/591,084, filed on Jul. 27, 2004.

(51) Int. Cl.
*G01G 9/00* (2006.01)

(52) U.S. Cl. .......................................................... 73/865
(58) Field of Classification Search ................... 73/865; 117/25.11, 25.12, 25.13, 210 R, 211, 210 C, 117/210 EM, 210 FD, 245; 236/44 C
See application file for complete search history.

(56) References Cited

U.S. PATENT DOCUMENTS

| | | | |
|---|---|---|---|
| 3,943,754 A | 3/1976 | Orr, Jr. | |
| 4,274,364 A * | 6/1981 | Forseth | 119/300 |
| 4,285,412 A | 8/1981 | Wirth | |
| 4,391,338 A | 7/1983 | Patashnick et al. | |
| 4,465,152 A | 8/1984 | Schmitter | |
| 4,548,288 A | 10/1985 | Komoto | |
| 4,609,061 A | 9/1986 | Jacobsson | |
| 4,815,314 A | 3/1989 | Plank | |
| 4,821,821 A | 4/1989 | Kelley | |
| 4,827,760 A | 5/1989 | Saito | |
| 4,846,293 A | 7/1989 | Li | |
| 5,025,619 A * | 6/1991 | Cannon | 119/300 |
| 5,056,050 A | 10/1991 | Fuchs et al. | |
| 5,428,964 A * | 7/1995 | Lobdell | 62/176.6 |
| 5,571,945 A | 11/1996 | Koutrakis et al. | |
| 5,850,968 A * | 12/1998 | Jokinen | 236/44 C |
| 5,869,788 A | 2/1999 | Gordon et al. | |
| 5,932,795 A | 8/1999 | Koutrakis et al. | |
| 6,122,954 A | 9/2000 | Bowers | |
| 6,151,953 A | 11/2000 | Patashnick et al. | |
| 6,205,842 B1 | 3/2001 | Patashnick et al. | |

(Continued)

OTHER PUBLICATIONS

International Search Report and Written Opinion on PCT application PCT/CA2005/000672 mailed Aug. 17, 2005.

(Continued)

*Primary Examiner*—Robert Raevis
(74) *Attorney, Agent, or Firm*—George A. Seaby

(57) ABSTRACT

Relatively accurate gravimetric analysis of airborne particulate matter in a sample is achieved by making gravimetric measurements of the sample on a microbalance in a closed chamber, continuously electronically monitoring air pressure, humidity and temperature in the chamber, continuously controlling humidity and temperature in the chamber, and combining the gravimetric measurement with measurements of air pressure, humidity and temperature in the chamber to make a buoyancy corrected determination of the mass of the particulate matter.

8 Claims, 3 Drawing Sheets

U.S. PATENT DOCUMENTS

| | | | |
|---|---|---|---|
| 6,477,888 B1 * | 11/2002 | Mizobe | 73/38 |
| 6,492,601 B1 * | 12/2002 | Cain et al. | 177/210 R |
| 6,504,112 B1 | 1/2003 | Luebke et al. | |
| 6,515,238 B1 | 2/2003 | Martens et al. | |
| 6,615,638 B1 | 9/2003 | Lochner et al. | |
| 6,651,480 B2 | 11/2003 | Patashnick et al. | |
| 6,784,381 B2 * | 8/2004 | Korpi | 177/210 FP |

OTHER PUBLICATIONS

Koistinen, Kimmo, Academic Dissertation, National Public Helath Institute, Kuopio, Finland, Apr. 20, 2002, pp. 1-81.

Koistinen et al., J Air Waste Management Assoc, 1999, vol. 49, pp. 1212-1220.

Koistinen et al., J Air Waste Management Assoc, 2002, vol. 52, pp. 134-139.

Schoonover et al., Anal. Chem., 1981, vol. 53, pp. 900-902.

Sartorius Micro and Ultra Micro Balances; Internet Website (1998) http://www.intinscales.com/sartorius_micro_balances.html.

Allen et al., J Air Waste Management Assoc, 2001, vol. 51, pp. 1650-1653.

Carlton, et al., Air Waste Management Assoc, 2002, vol. 52, pp. 506-510.

US-EPA Quality Assurance Guidance Document 2.12, U.S. Environmental Protection Agency, vol. II Part II, Nov. 1998, Research Triangle Park, NC 27711 USA.

Wunderli et al., Anal. Bioanal. Chem., 2003, vol. 376, pp. 384-391.

Lawless et al., J. Air & Waste Management, 1999, vol. 49, pp. 1039-1049.

Code of Federal Regulations, Title 40, Part 86, vol. 16, Jul. 1, 2002 (40CFR86. 1312-2007, pp. 233-236).

Espacenet abstract of DE 3106564, published Sep. 16, 1982, Sartorius GMBH.

Espacenet abstract of DE 3106534, published Oct. 28, 1982, Sartorius GMBH.

\* cited by examiner

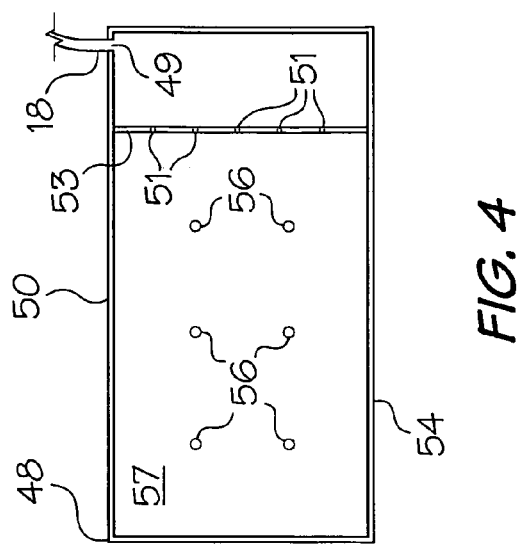
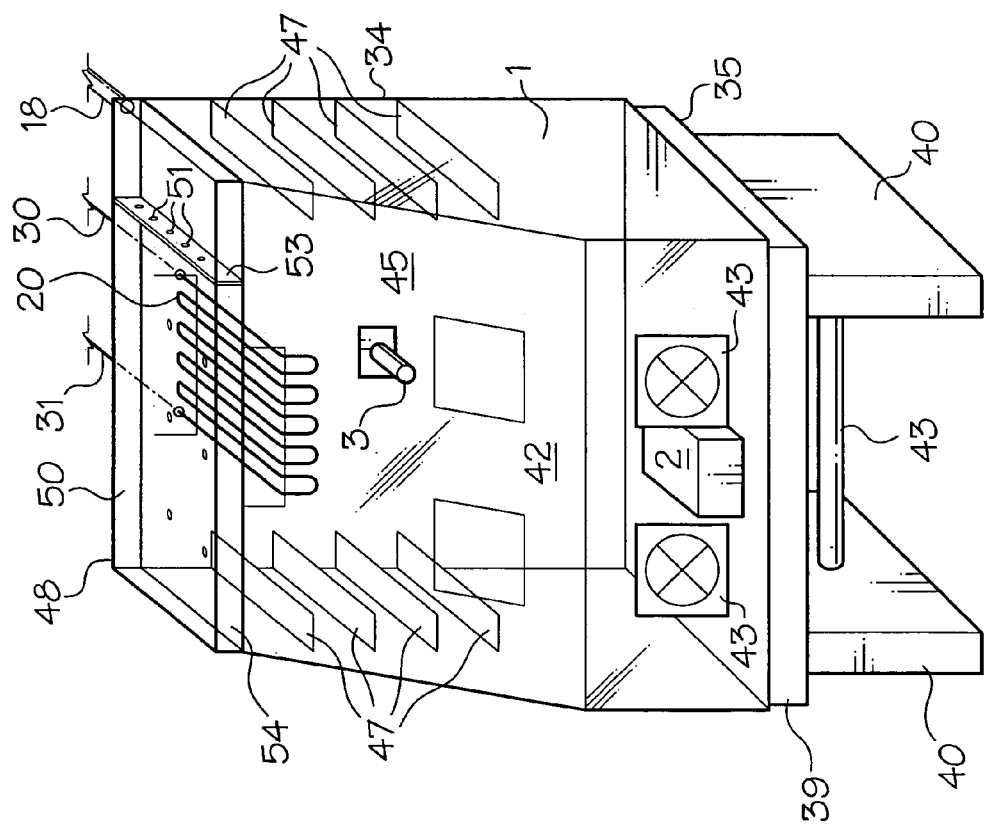

US 7,357,045 B2

BUOYANCY-CORRECTED GRAVIMETRIC ANALYSIS SYSTEM

CROSS REFERENCE TO RELATED APPLICATION

This application claims priority on U.S. Provisional Patent Application 60/591,084 filed Jul. 27, 2004

BACKGROUND OF THE INVENTION

Field of the Invention

This invention relates to a system and method for determining the mass of particulate matter, and in particular airborne particulate matter.

When conducting the gravimetric analysis (mass determination) of airborne particulate matter, the mass of individual filters is determined before and after the filters are exposed to an atmosphere containing such matter. Many environmental factors cause unacceptable errors in the mass determination including air density of airborne particulate matter. Measurements of very small particle masses (less than 0.1 mg) may require a correction for the influence of air density, depending on the required level of accuracy. This is called an air buoyancy correction.

Buoyancy corrections can be made in two ways. The classical method is to calculate air density by measuring air temperature, air pressure and relative humidity in a balance room at the time of mass determination. Air density is then used to determine the buoyancy correction. An alternate method is to correct for air buoyancy using a mass artifact (also known as a "buoyancy standard"), in which case air density does not need to be known [Wunderli et al, Anal. Bioanal. Chem. 376: 384-392, (2003)]. However, the artifact method appears to be inapplicable to the measurement of airborne particulate matter, due to the difficulty in estimating sample volume with sufficient accuracy.

The classical method is appropriate in theory, but it requires suitable equipment for simultaneous monitoring of air pressure, temperature and humidity, in order to determine air density at the precise time of mass determination. Current US-Environmental Protection Agency (EPA) guidelines for mass determination of airborne particulate matter do not require measurement of air density, and therefore disregard buoyancy corrections. At present, there is no apparatus, product or process for effecting buoyancy-corrected gravimetric analysis of airborne particulate matter, while at the same time meeting or exceeding all other requirements of the US-EPA guidelines (stable relative humidity, stable temperature, low airborne particle concentrations, elimination of electrostatic charge, and physical stability).

Recently there has been a trend towards using controlled environmental chambers to meet US-EPA guidelines, because this approach can be less costly and more effective than attempting to control environmental parameters inside an entire room. However, publications relating to existing environmental chambers designed to meet US-EPA guidelines indicate that they do not include the capacity to make buoyancy corrections [Allen et al (2001) and Carlton et al (2002), Journal of the Air and Waste Management Association, Vol. 51, pp 1650-1653 and Vol. 52, pp. 506-510, respectively]. Accordingly, a need still exists for means to make buoyancy corrected mass determination of particulate matter.

BRIEF DESCRIPTION OF THE INVENTION

The object of the present invention is to meet the above defined need by providing a relatively simple method and apparatus for effecting buoyancy corrected determination of the mass of particulate material.

According to one aspect, the invention relates to a system for determining the mass of a sample containing particulate matter comprising:
a housing defining a chamber;
a microbalance in said chamber for measuring the mass of a sample;
a source of air under pressure for supplying air to said chamber;
humidifier means for humidifying air from said source of air;
heating and cooling means in said chamber for changing the ambient temperature in said chamber;
sensor means for continuously monitoring the pressure, temperature and relative humidity in said chamber; and
control means connected to said sensor means and to said source of air, said humidifier means and said heating and cooling means for controlling the flow of air to said chamber, and the relative humidity and temperature in said chamber,
whereby measurements of the pressure, temperature and humidity can be combined with gravimetric measurements made using the microblance to provide buoyancy corrected determinations of the mass of a sample containing particulate material.

According to another aspect, the invention relates to a method of determining the mass of a sample of particulate matter comprising the steps of:
making gravimetric measurements of a sample containing particulate matter in a closed chamber;
continuously controlling humidity and temperature in the chamber;
continuously monitoring the air pressure, humidity and temperature in the chamber while making the gravimetric measurements, and
using the gravimetric measurements in combination with the measurements of the air pressure, humidity and temperature to make a buoyancy corrected determination of the mass of the sample.

BRIEF DESCRIPTION OF THE DRAWINGS

The invention is described below in greater detail with reference to the accompanying drawings, which illustrate a preferred embodiment of the invention, and wherein:
FIG. 3 is a schematic, isometric view of the gravimetric apparatus of FIG. 2;
and
FIG. 4 is a cross section taken generally along line 4-4 of FIG. 2.

DESCRIPTION OF THE PREFERRED EMBODIMENT

Figure 1:
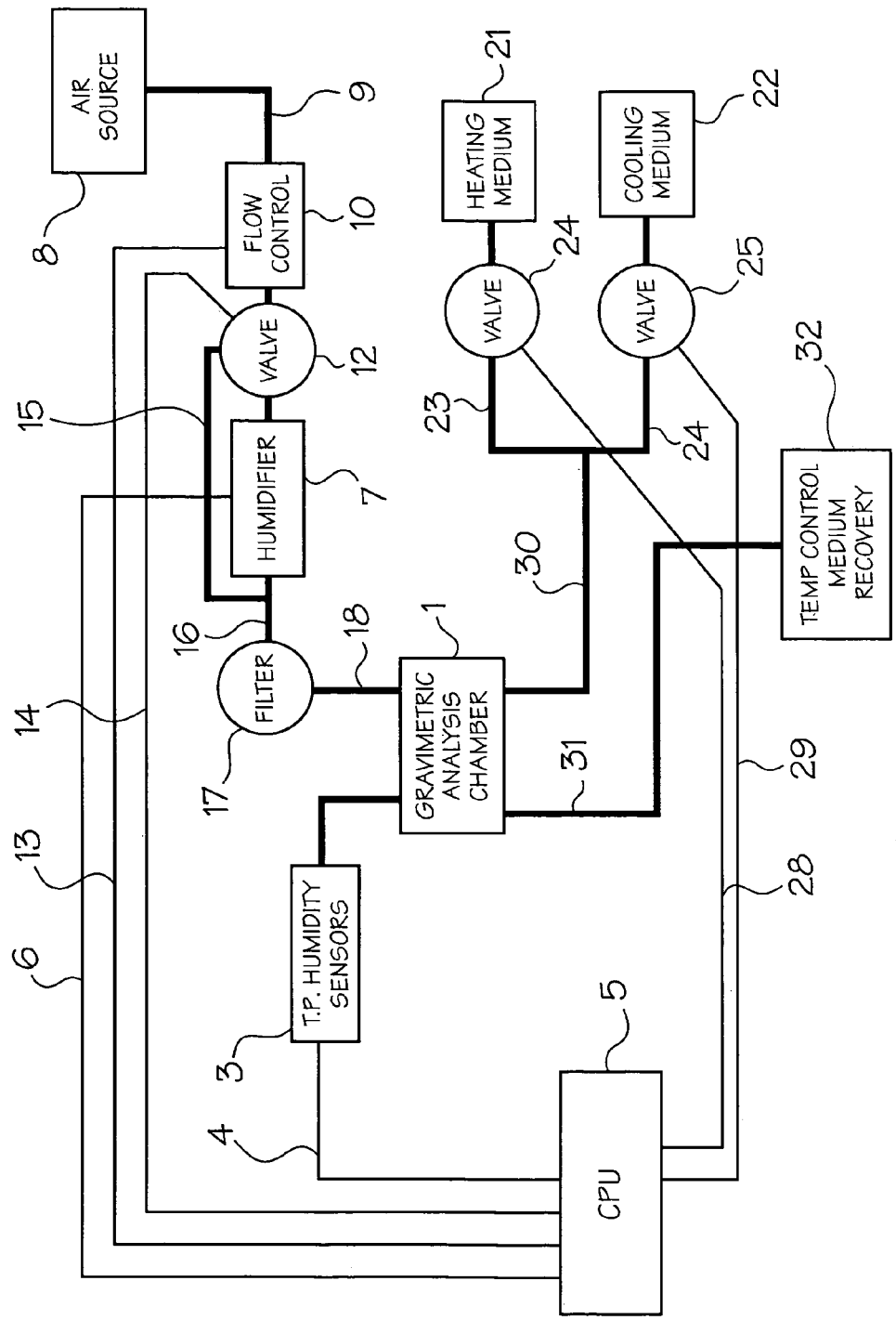
FIG. 1 is a block diagram of a gravimetric analysis system in accordance with the invention.

Referring to FIG. 1, the preferred embodiment of the gravimetric analysis system includes a gravimetric analysis chamber 1 containing a microbalance 2 (FIGS. 2 and 3) for making gravimetric measurements. A suitable microbalance is the Mettler-Toledo UMX2 balance. A disc-shaped air filter (not shown) is placed on the microbalance. The filters in the present case are 37 or 47 mass PFTE members available from Pall Corporation, East Hill, N.Y. The mass of the filters is determined before and exposing the filters to an atmosphere containing particulate matter. Air temperature, pressure and humidity in the chamber 1 are continuously monitored, and the air temperature and humidity are continuously controlled. For monitoring, a temperature, humidity and pressure sensor unit 3 is provided in the chamber 1. A suitable sensor unit is a Vaisala PTB100A analog barometer available from Vaisala, Oyj, Vantaa, Finland and a Dew-Trac® Humidity Transmitter, EdgeTech Model 200 available from EdgeTech, Milford, Mass., which includes a sensor probe, an electronic control unit and an ambient temperature kit. The outputs of the sensor unit 3 are fed via line 4 to a central processing unit (CPU) 5, i.e. the ambient pressure, dew point temperature, ambient temperature and equivalent relative humidity are routed to a data acquisition control system at one minute intervals. In this case, the control system is an ADAM 5000E (Advantech Co. Ltd., Carlsbad, Calif.). The ADAM control system transmits the data to a software program (Labtech Control version 12.1.2 (2001) from Measurement Computing Corporation, Middleborough, Mass.) which continuously receives, processes and records the data for storage on a hard drive.

The CPU 5 is connected by line 6 to a humidifier 7. Dry air from a compressed air tank 8 flows through a Teflon® tube 9, a mass-flow controller 10 and a three way valve 12 to the humidifier 7. A suitable flow controller 10 is Model GFC1715 available form Aalborg Instruments & Controls Inc., Orangeburg, N.Y. The humidifier 7 and the flow control 10 are connected to the CPU 5 by lines 13 and 14, respectively. If the humidity is low, the ADAM controller triggers the solenoid valve 12 to direct the air through the humidifier 7, which is in the form of a closed, heated water tank, in which the air takes up water as it passes over the water surface. If the humidity in the chamber 1 is high, the solenoid vale 12 is operated to direct dry air through a tube 15 which bypasses the humidifier 7 and directs air to a humidifier outlet tube 16. Dry or moist air in the tube 16 passes through a filter 17 and a tube 18 into the chamber 1.

The temperature in the chamber 1 is controlled by circulating hot or cold water through a heat exchanger in the form of a stainless steel coil 20 (FIGS. 2 and 3) in the top of the chamber. Hot and cold water is fed from sources 21 and 22, respectively through tubes 23 and 24 containing solenoid valves 25 and 26, respectively. The valves 25 and 26 are connected to the CPU 5 by lines 28 and 29, respectively. After passing through the valves 25 and 26, the heating and cooling mediums are mixed in tube 30, which is connected to the coil 20 in the chamber. Temperature control medium is discharged from the coil 20 via a tube 31 connected to a medium recovery vessel 32.

Figure 2:
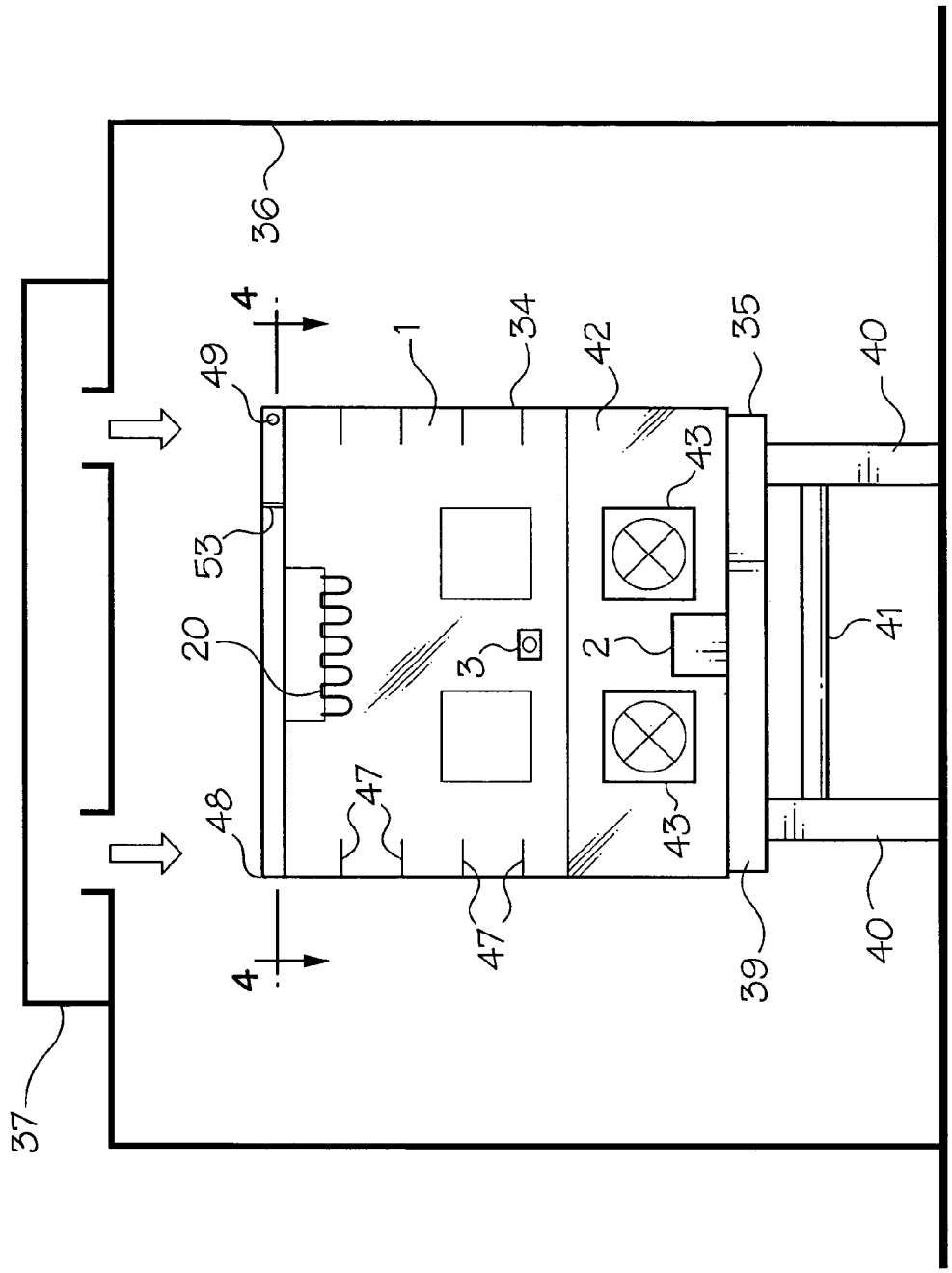
FIG. 2 is a schematic front view of a clean room and a gravimetric analysis apparatus used in the system of FIG. 1.

With reference to FIGS. 2 to 4, the Plexiglas® walls of the housing 34 form the chamber 1. The housing 34 is mounted on a table 35 in a soft-walled Class 100 clean room 36 equipped with a high efficiency particulate arrestance filtration system 37, which operates twenty-four hours a day. A high voltage (7 kV) Mettler-Toledo point de-ionizer (not shown) in the chamber 1 ionizes surrounding air to create ozone, which effectively removes static charge from the filters in the system 37. Two polonium-210 anti-static strips can also be located in the chamber 1 if an alternate de-ionizing approach is more appropriate for a given application. The table 35 weighs 700 lbs. and includes a top 39 and legs 40 all of which are formed of marble and a stainless steel crossbar 41 extending between the legs 40.

The housing 34 includes a front wall 42 with access ports 43, side walls 44 and a rear wall 45. Sample holding shelves 47 are provided on the interior of the side walls 44. The top of the housing 34 is defined by a rectangular inlet manifold 48 for receiving air from the tube 18. Air is introduced into the housing 34 via an inlet 49 in the rear wall 50 of the manifold 48. The air entering the manifold 48 passes through openings 51 in a partition 53 extending between the rear wall 50 and a front wall 54, and then through vertical orifices 56 in the bottom wall 57 of the manifold.

In operation, the microbalance 2 is used to make mass measurements manually with a readability of 0.1 μg. The measurement data from the microbalance 2 may be transmitted electronically to the CPU 5 using BalanceLink software (Mettler-Toledo) or entered into an electronic spreadsheet from handwritten notes. The microbalance 2 is programmed to auto-calibrate at the same time (2 am) each day.

The four atmospheric parameters required to calculate air density (relative humidity, pressure, temperature and dew point temperature) are recorded at one minute intervals by the Labtech software. Air density (AD) is calculated using the equation:

$$AD = (3.484P - 0.80439726 \times 10^{((7.5Tdp)/(237.3+Tdp))}) \div (T + 273.15)$$

where P=pressure (kPa), T=temperature (° C.) and Tdp=dew point temperature (° C.).

By calculating air density at the precise time of measuring the mass of a sample and at the precise time of auto calibration, the buoyancy correction equation can then be applied to the measured mass of the sample. The buoyancy correction equation is:

$$Mp = Wp(1 - pa_r/Pr)/(1 - pa/Pp)$$

where Mp is the corrected mass of the sample, Wp is the weighing value of the sample, Pp is the density of the sample, Pr is the density of a reference weight, pa is the air density at the time of mass measurement and par is the air density at the time of the last auto-calibration.

A custom software application was written in Microsoft Access to combine computationally the atmospheric parameters in the chamber 1 (recorded using the Labtech software) with the mass measurement data (recorded using the BalanceLink microbalance software), and to calculate the final buoyancy-corrected mass of the sample.

The invention claimed is:
1. A system for determining the mass of a sample containing particulate matter comprising:
   a clean room;
   a housing defining a chamber in said clean room;
   a microbalance in said chamber for measuring the mass of a sample;
   a source of air under pressure for supplying air to said chamber;
   humidifier means for humidifying air from said source of air;
   heating and cooling means in said chamber for changing the ambient temperature in said chamber;
   sensor means for continuously monitoring the ambient air pressure, the dew point temperature, the relative humidity and the ambient temperature in said chamber; and
   control means connected to said sensor means and to said source of air, said humidifier means and said heating and cooling means for controlling the flow of air to said chamber, and the relative humidity and ambient temperature in said chamber, whereby measurements of the ambient air pressure, ambient temperature and dew point temperature inside the chamber can be combined with gravimetric measurements made using the microbalance to provide buoyancy corrected determinations of the mass of a sample containing particulate material.

2. The system of claim 1, wherein said housing includes a manifold for receiving the air under pressure and for distributing the air into said chamber.

3. The system of claim 2, including bypass means for feeding air from said source of air under pressure directly to said chamber without humidification.

4. The system of claim 3, wherein said heating and cooling means includes a source of heating medium, a source of cooling medium, and coil means in said chamber for circulating medium through the chamber.

5. The system of claim 1, wherein said control means includes a central processing unit connected to said microbalance, said humidifier means, said heating and cooling means, and said sensor means.

6. The system of claim 1, wherein said clean room is a Class 100, soft-wailed clean room.

7. A method of determining the mass of a sample of particulate matter comprising the steps of:
making gravimetric measurements of a sample containing particulate matter in a closed chamber;
continuously controlling relative humidity and ambient temperature inside the chamber;
continuously monitoring the ambient air pressure, the dew point temperature, the relative humidity and the ambient temperature in the chamber while making the gravimetric measurements, and
using the gravimetric measurements in combination with the measurements of the ambient air pressure, the dew point temperature, and the ambient temperature in the closed chamber to make a buoyancy corrected determination of the mass of the sample.

8. The method of claim 7, wherein the ambient air pressure, the dew point temperature, the relative humidity and the ambient temperature are continuously monitored at one minute intervals.

* * * * *